United States Patent [19]

Bechtel

[11] Patent Number: 4,932,267
[45] Date of Patent: Jun. 12, 1990

[54] FLEXURE COUPLING

[75] Inventor: Friend K. Bechtel, Moscow, Id.

[73] Assignee: Metriguard, Inc., Pullman, Wash.

[21] Appl. No.: 368,172

[22] Filed: Jun. 19, 1989

[51] Int. Cl.$^5$ .............................................. G01N 3/20
[52] U.S. Cl. ...................................... 73/852; 464/81;
464/100
[58] Field of Search .................... 464/81, 82, 100, 160;
403/220, 291; 73/849, 852

[56] References Cited

U.S. PATENT DOCUMENTS 3,196,672  7/1965  Keller .
4,708,020  11/1987  Lau et al. .............................. 73/852

FOREIGN PATENT DOCUMENTS 2837395  2/1980  Fed. Rep. of Germany ........ 464/82
0781438  11/1980  U.S.S.R. .................................. 464/82
00752485  7/1956  United Kingdom .................. 464/81
2017259  10/1979  United Kingdom .................. 464/82

OTHER PUBLICATIONS

Metriguard, Inc. Brochure "CLT—Continuous Lumber Tester".
SKF brochure "Bearing Failures and Their Causes," Mar. 1980 (pp. 16, 17).

Primary Examiner—Robert R. Raevis
Attorney, Agent, or Firm—Wells, St. John & Roberts

[57] ABSTRACT

A flexure coupling includes a backing plate and an adjacent hub, the backing plate being adapted to be mounted to a first machine member and the hub being adapted to be mounted to a second machine member. The hub is supported on the backing plate by a plurality of equiangularly positioned radial springs that permit compliant torsional movement of the hub relative to the backing plate. The springs prevent relative axial or longitudinal translational movement between the hub and backing plate, as well as relative radial movement. Substitution of the flexure coupling for conventional bearings eliminates the problem of false brinelling that results from vibration of stationary bearings.

19 Claims, 3 Drawing Sheets

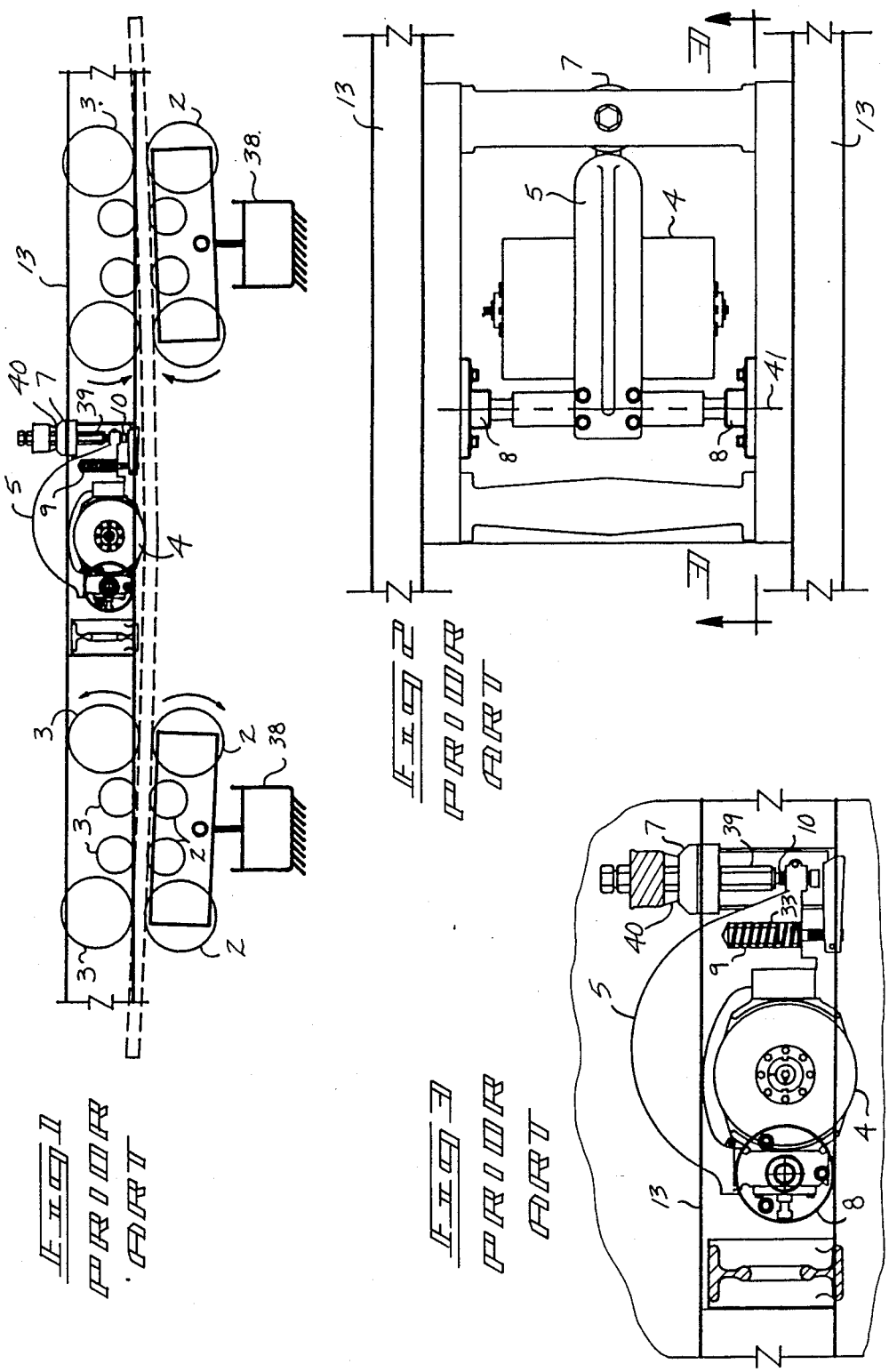

FLEXURE COUPLING

TECHNICAL FIELD

This disclosure relates to a compact mechanical flexure coupling that operates in rotation about a reference axis. The flexure coupling is used to support a second member of a machine relative to a first member so that, with selected compliance, small rotations of the second member relative to the first member can occur about the reference axis. Radial movement and axial and longitudinal translation of the second member relative to the first member at the reference axis are prevented.

BACKGROUND OF THE INVENTION

In the sorting of lumber according to its bending stiffness, the most commonly used machines and processes for high speed production facilities involve bending of boards as they are tested in a machine especially constructed for this purpose. Such machines use a series of rollers that bend each board in opposite directions as it passes longitudinally through the machine. Background information on such testing equipment and processes can be found in U.S. Pat. No. 3,196,672 (Keller), which is hereby incorporated into this disclosure by reference.

The machine described in the Keller patent disclosure causes substantially constant bending deflection of boards by a measuring transducer assembly that detects the force applied to each board by a load point on the transducer assembly. For the lumber testing machine example, the load point consists of a transverse line contact between a force roller and each board as it is bent. The force roller is part of the detecting transducer assembly. At high machine speeds, constant lumber deflection and fixed position of the transducer assembly is vital because they substantially remove the inertias of the transducer assembly from affecting the bending measurement.

The transducer assembly is located relative to the machine frame at two longitudinal reference points along the length of the transducer assembly. At one reference point two roller bearings on a common transverse bearing reference axis fix the transducer assembly in translation to the machine frame. At the other reference point, the transducer assembly rests against an electronic load cell used to measure force applied by the transducer assembly to the load cell. By this means, the force applied by the load point force roller to the lumber can be detected.

These reference points at both locations along the length of the transducer assembly are intended to fix the transducer assembly in translation so that the load point on the transducer assembly remains substantially constant relative to the machine frame. There is, however, a minute compliance required at the load cell reference point for a measurement of force to be made. For load cells used in the commercial implementation of the Keller patent disclosure, this compliance is about $33.3 \times 10^9$ feet/pound ($2.28 \times 10^9$ meter/newton). Roller bearings are conventionally used in these machines at the bearing reference axis, so that as load cell compression occurs there will be no torsional restraint of the transducer assembly relative to the machine frame. If the bearings are properly adjusted with a small preload, they will allow slight angular movement of the transducer assembly about the bearing reference axis and prevent radial motion or axial or longitudinal translation between the transducer assembly and machine frame at that point.

Unfortunately, roller bearings operating in this mode are subject to brinelling failure (actually known as "false brinelling") caused by vibration with bearings stationary. This can be predicted. And, it is borne out in practice, as observed by the failure mode of these bearings. Bearings exhibiting false brinelling wear patterns will loosen as they wear, thereby allowing translational motion in their support of the transducer assembly which leads to accuracy problems in the load measurement. Further, if the bearings are tightened by adjustment to remove the translational freedom, the wear patterns serve as detent positions in the bearings and cause nonlinear restrictions in rotation of the transducer assembly about the bearing reference axis, and this also reduces accuracy. Another problem with the bearings now used has been the difficulty in rigidly attaching their inner races to the transducer assembly; any lack of translational rigidity at this point leads to accuracy and repeatability problems.

In the application of sorting lumber, one orientation of the transducer assembly requires a spring to maintain positive pressure of the transducer assembly against the load cell, thus countering the effect of gravity which, in the absence of the spring, would cause the assembly to pivot around the bearing reference axis and fall free of the load cell reference point. Constraining the spring so that it does the required job of preloading the transducer assembly against the load cell with negligible friction has been a continuing problem of this design. The sides of the spring can rub against the spring restraint, and the resulting friction leads to repeatability problems in calibrating the system's zero point.

BRIEF DESCRIPTION OF THE DRAWINGS

The preferred embodiment of the invention is illustrated in the accompanying drawings, in which:

FIG. 1 is a schematic longitudinal side view of one lumber testing section in the prior art continuous lumber tester;

FIG. 2 is an enlarged plan view of the central portion of the section shown in FIG. 1;

FIG. 3 is a sectional view taken along line 3—3 in FIG. 2;

DETAILED DESCRIPTION OF THE PREFERRED EMBODIMENT

Figure 4:
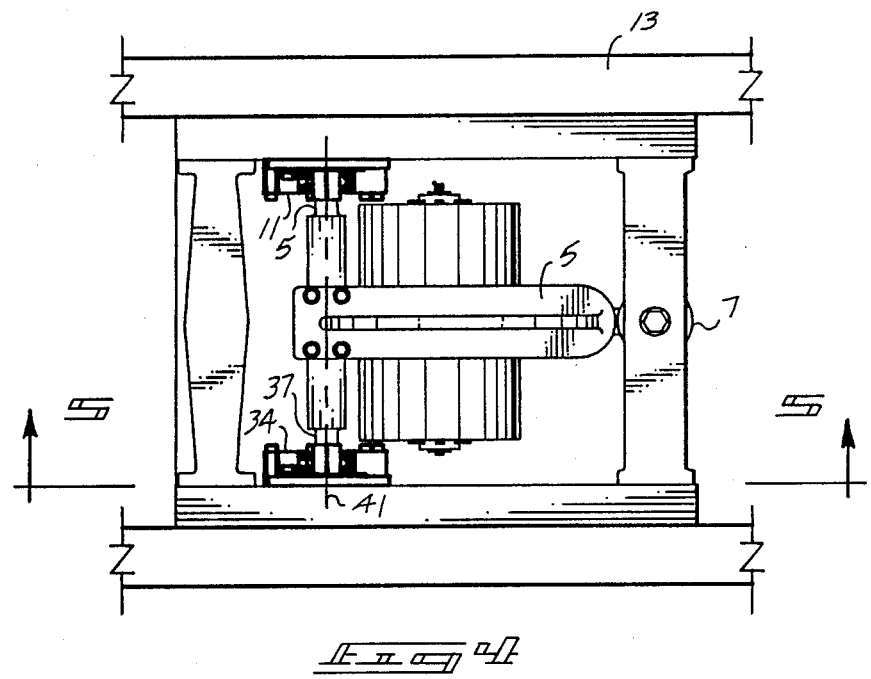
FIG. 4 is a view similar to FIG. 2, showing the present improvement.

The following disclosure of the invention is submitted in compliance with the constitutional purpose of the Patent Laws "to promote the progress of science and useful arts" (Article 1, Section 8).

The machine for which this flexure coupling was developed is entitled "CLT-Continuous Lumber Tester", produced by Metriguard Inc., of Pullman, Wash. The CLT machine is a high speed production-line system based on the Keller U.S. Pat. No. 3,196,672. It is responsible for most of the machine stress rated lumber production today in North America.

FIG. 1 schematically illustrates the first of two bending sections in a prior art CLT machine. FIGS. 2 and 3 are enlarged views taken in the area of the transducer assembly. When a board 1 enters the space between upper and lower opposed clamp rollers 2 and 3, it forces the lower clamp rollers 2 to move slightly downward against air supports 38 on the machine frame. The lower clamp rollers 2 squeeze the board against the upper clamp rollers 3, whose axes are substantially fixed relative to longitudinal machine frame members 13, thereby defining the vertical position of the lumber at each end of a test span.

The load point force roller 4 at the center of the test span is substantially fixed in translational position by a force beam 5 which supports it. The force beam 5 is itself referenced the machine frame members 13 at one end of the force beam by a load cell 7 and at the other by two roller bearings 8. The bearings 8 are located on a common transverse bearing reference axis 41. Near the load cell reference point, a null spring 9 holds the force beam upwardly to provide a positive upward biasing force on load cell 7 even in the absence of lumber. This biasing force is treated as a tare force and is removed from the resulting measurements by an electronic zero adjustment. Because of the friction of null spring 9 against the spring restraint bore 33 in the force beam 5, repeatability of the electronic zero adjustment has been a consistent problem. An adjustment screw 10 makes contact with a spacer 39 rigidly attached to the load cell 7. The load cell is itself rigidly attached to the machine frame by a support bracket 40. The adjustment screw 10 allows the force beam 5, and hence the load point force roller 4, to be positioned as desired to control the amount of lumber deflection or bending.

The second bending section of a CLT machine (not shown) is similar to the first, but it bends the boards upwardly instead of downwardly. In the second bending section, the load point force roller, force beam, load cell, and adjustment screw are all located below the board rather than above it. All of these components are formed as mirror images about a horizontal plane relative to the corresponding components illustrated in FIGS. 1-3. The null spring 9 is unnecessary in the second bending section because gravity accomplishes the purpose of maintaining a positive downward biasing force on the load cell.

Figure 5:
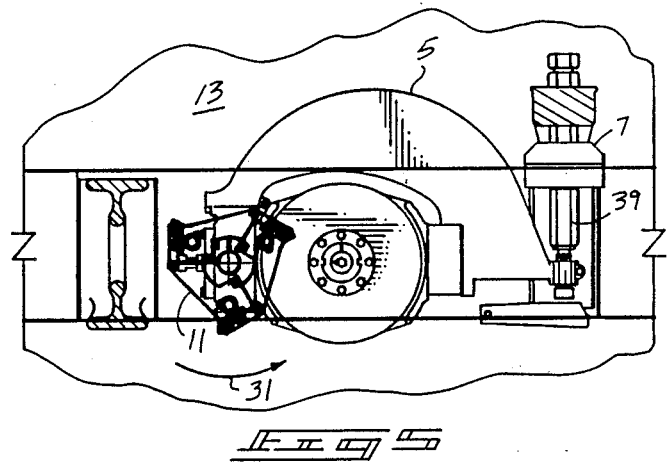
FIG. 5 is a sectional view taken along line 5—5 in FIG. 4.

FIGS. 4 and 5 illustrate the same machine areas as FIGS. 2 and 3. The improved flexure couplings 11 and 34 of the present disclosure have replaced the bearings 8, and the null spring 9 has been deleted. A left-handed flexure coupling 11 is mounted between the left side of the machine frame and a left stub shaft 15 on the bearing reference axis 41 of the force beam 5. A right-handed flexure coupling 34 is mounted between the right side of the machine frame and a right stub shaft 37 on the bearing reference axis 41 of the force beam 5. The flexure couplings 11 and 34 are compact, and fit in the same locations as the bearings 8 (FIGS. 1-3) they replace.

The improved flexure coupling provides a compliant torsional connection between first and second members of a machine, such as the CLT machine used for testing lumber. It basically comprises a hub 16 that is adapted to be fixed to a second member of a machine. The hub 16 includes a central reference axis about which very limited angular movement of one machine member relative to the other must be accommodated.

A backing plate 12 is located axially adjacent to the hub 16. It is adapted to be fixed to the first member of the machine and is intersected by the reference axis.

At least three flexible plate springs 18 extend radially outward from the hub 16. Each spring 18 has an inner radial end fixed to the hub 16 and an outer radial end fixed to the backing plate 12. Springs 18 permit limited relative angular movement between the hub 16 and backing plate 12 to be accommodated about the reference axis while preventing relative radial or axial movement between them.

In the preferred embodiment, the hub 16 is physically spaced adjacent to the backing plate 12. Hub 16 is preferably a split collar having a central cylindrical bore that is adapted to receive and clamp a shaft extending from the second machine element. A plurality of standoffs, equal in number to the number of springs, are included within the backing plate structure. Each standoff has a spring mounting surface oriented radially relative to the reference axis. The outer radial end of the respective springs are fixed to the spring mounting surfaces of the standoffs. A supporting section of the standoff 17 adjacent to the spring mounting surface is bendable by an amount sufficient to accommodate resultant radial shortening of the spring 18 caused by limited relative angular movement between the hub 16 and backing plate 12. The supporting section of each standoff 17 adjacent to its spring mounting surface is axially spaced from the remainder of the backing plate 12.

Figure 7:
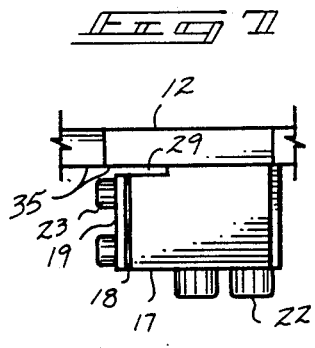
FIG. 7 is a fragmentary plan view of the flexure coupling backing plate and standoff as viewed along line 7—7 in FIG. 6.
Figure 6:
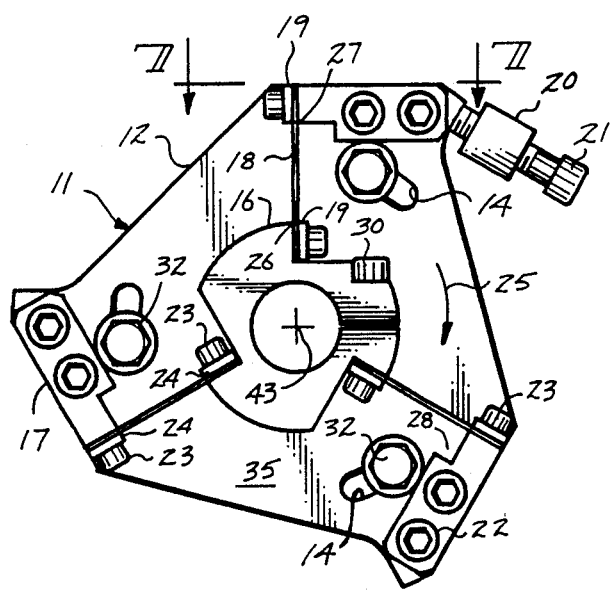
FIG. 6 is an elevation view of one flexure coupling.
Figure 8:
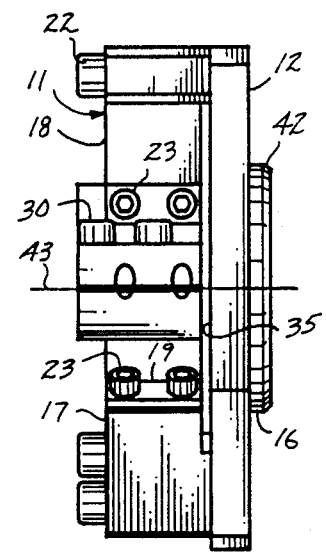
FIG. 8 is an end view taken from the right in FIG. 6, minus the optional adjustment ear and backing plate holding screws.

FIGS. 6-8 illustrate a left-handed preferred embodiment of the flexure coupling 11 constructed according to the present invention. The right-handed flexure coupling 34 shown in FIG. 4 has mirror symmetry with the left-handed embodiment.

The flexure coupling 11 consists of a backing plate 12, a hub 16, three standoffs 17, three springs 18, six spring washers 19, an optional adjustment ear 20 and adjustment screw 21, plus the fasteners required for assembly. A pilot cylinder protrusion 6 on backing plate 12 indexes the flexure coupling to the machine frame as did the pilot on the mounting flange of the bearing 8 which it replaces. Slotted holes 14, located on backing plate 12 at the same radius as mounting holes for the bearing flange, allow the flexure coupling 11 to be rotated with respect to the machine frame member 13 in a continuum of adjustment positions within the range of the slotted holes 14.

As previously described, the backing plate allows mounting of the flexure interchangeably with the bearing that it replaces. Normally the pilot cylindrical protrusion 6 at the rear of backing plate 12 would have a chamfer 42 to allow easier installation.

The backing plate 12 mounts to one machine frame member 13, and the hub 16 slips over the stub shaft 15 on the bearing reference axis 41 of the force beam 5. When mounted in the machine, a flexure axis 43 (FIGS. 6 and 8) coincides with the bearing reference axis 41 of FIGS. 2 and 4.

The standoffs 17 are fastened rigidly to the backing plate 12 by cap screws 22. The springs 18 are fastened rigidly to the hub 16 and standoffs 17 with cap screws 23 through washers 19 made from steel plates.

Handedness of the hub, standoffs, and backing plate is arranged so that at opposite ends of the springs, the cap screws 23 enter from opposite sides. This reduces friction and hence hysteresis or energy losses at the spring attachment points 24 during rotation of the hub 16 relative to the backing plate 12 in a preferred direction 25. In FIG. 6, the preferred direction of flexing occurs when the hub 16 rotates clockwise in the direction of arrow 25 with respect to the backing plate 12. In this case it will be seen that each spring 18 bends around an edge 26 of the hub 16 at one radial end of the spring and around an edge 27 of a standoff 17 at the other radial end of the spring. The edges of the hub 16 and standoffs 17 are slightly rounded to reduce stress in the spring 18 at these points.

A relief 28 is cut in the portions of the standoffs 17 attached to the springs 18 so that a controlled small amount of bending or flexure can occur in the standoffs 17 as the springs 18 are flexed, thereby changing the spring length in the radial direction. The standoffs 17 are each undercut at 29 on the backing plate interface surface 35 in the region of the spring attachment. This reduces friction as the standoffs 17 flex, and hence energy loss in the area between the standoffs 17 and the backing plate interface surface 35.

The rotational compliance of the flexure coupling can be preset by selecting a different thickness or shape of clock spring steel for the springs 18. It is seen that the springs 18 are easily replaceable in the event they are accidentally over-stressed by too much relative rotational movement between hub 16 and backing plate 12.

The rotational attachment position of the hub 16 to the left stub shaft 15 of the force beam is easily adjusted by means of the clamping cap screws 30, which when loosened allow relative rotational and axial motion between these two elements. When tightened, they assure rigid frictional clamping contact between the hub 16 and the stub shaft 15.

Referring to FIG. 5, it is seen that adjustment of the left flexure coupling 11 by rotating the backing plate 12 in a direction 31 relative to the machine frame 13 and a similar adjustment of the right flexure coupling 34 will cause torque to be applied to the force beam 5 in direction 31 to load the load cell 7 as desired. A tare load on the load cell can be preset in this fashion. The amount of flexing, and hence tare load, applied by each flexure coupling through the force beam 5 to the load cell 7 can be adjusted easily by means of either an optional adjustment ear 20 and adjustment screw 21 (FIG. 6) or by application of turning force to one of the standoffs 17 to apply torque to the backing plate 12 and cause it to rotate within the range of slotted holes 14. When the backing plate 12 is in the proper rotational position, relative to the machine frame, the backing plate holding screws 32 are tightened.

The rotational compliance and maximum stress on the springs for a given relative rotation between hub 16 and backing plate 12 is selectable by choosing different spring elements for the flexures. For lumber testing purposes, a practical choice of spring elements causes the effective compliance due to the flexure couplings 11 and 34 as seen at the load cell support point to be very much greater than the load cell compliance. Consequently, the gain setting for force measurement at the load cell 7 is affected by only a very small and negligible amount; however, even if the effect were not negligible, linearity of the springs would allow a compensating recalibration of the load cell gain.

The flexure couplings 11, 34 replace both the bearings 8 and the null spring 9 of the prior art apparatus shown in FIGS. 1–3. Experiments have shown that the features described above cause a very repeatable tare on the load cell 7. This repeatability is attributed to the reduced friction and hence reduced hysteresis or energy loss below the friction of the null spring 9 that is replaced. Rigidity in the radial direction of the flexure couplings is assured because of the high stiffness of the clock spring steel spring elements in tension and their arrangement at equiangular 120 degree intervals about the circle of the flexure coupling. Rigidity in the axial direction is assured by applying sufficient torque to the cap screws 22 and 23 in the assembly. There is no wear-out mechanism of the flexure couplings 11 and 34 in this application as opposed to the false brinelling of the bearings 8 they replace.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims appropriately interpreted in accordance with the doctrine of equivalents.

I claim:

1. A flexure coupling for providing a compliant torsional connection between first and second members of a machine to accommodate limited angular movement of one machine member relative to the other, comprising:

a backing plate adapted to be fixed to a first member of a machine;

a hub adapted to be fixed to a second member of the machine at a location axially adjacent to the backing plate, the hub having a reference axis intersecting the backing plate;

at least three flexible plate springs lying along angularly spaced planes that intersect the reference axis and extending radially outward from the hub, each spring having an inner radial end fixed to the hub and an outer radial end fixed to the backing plate, whereby limited relative angular movement between the hub and backing plate can be accommodated about the reference axis while preventing relative radial or axial movement between them.

2. The flexure coupling of claim 1 wherein the hub is a split collar having a central cylindrical bore adapted to receive and clamp a shaft extending from the second member of the machine.

3. The flexure coupling of claim 1, wherein the backing plate further comprises:

a plurality of standoffs equal in number to the number of flexible plate springs, each standoff having a spring mounting surface oriented radially relative to the reference axis and having the outer radial end of one flexible plate spring fixed thereto, a supporting section of the standoff adjacent to the spring mounting surface being bendable by an amount sufficient to accommodate resultant radial shortening of the spring caused by limited relative angular movement between the hub and backing plate.

4. The flexure coupling of claim 3 wherein the supporting section of each standoff adjacent to the spring mounting surface is axially spaced from the remainder of the backing plate.

5. In a machine having first and second members requiring compliant torsional coupling relative to one another about a reference axis to accommodate limited angular movement of one machine member relative to the other, an improved flexure coupling comprising:

a rigid backing plate transversely intersected by the reference axis, the backing plate having a surface that is perpendicular to the reference axis;

first mounting means for fixing the backing plate to the first member;

a hub located axially adjacent to the surface of the backing plate;

second mounting means for fixing the hub to the second member; and at least three flexible plate springs, each spring having an inner and outer radial end fixed respectively to the hub and backing plate, the springs being equiangularly positioned about the reference axis to accommodate limited relative angular movement between the first and second members about the reference axis while preventing relative radial or axial movement between them.

6. The machine of claim 5 including a second improved flexure coupling that is a mirror image of the first flexure coupling, the two flexure couplings being located at opposite sides of the second member to support it relative to the first member.

7. The machine of claim 5 in the form of a continuous lumber tester, the first member being the frame of the continuous lumber tester and the second member being a force beam having opposite longitudinal ends interconnected to the frame by a load cell at one of its ends and by a pair of the flexure couplings positioned at opposite axial sides of the force beam along the reference axis.

8. A flexure coupling for providing a compliant torsional connection between first and second members of a machine about a reference axis while maintaining rigid radial and axial translational coupling between them, the flexure coupling comprising:

a backing plate;

a hub;

a plurality of at least three standoffs each spaced radially from the hub, and a plurality of at least three springs, one spring for each standoff;

the backing plate being rigid and centered on the reference axis, the backing plate having mounting means for rigidly fixing it to the first member of the machine, the mounting means allowing for rotational adjustment of the backing plate relative to the first member of the machine, about the reference axis, the backing plate having additionally a means for rigidly mounting the standoffs to it;

the hub being a cylinder with a central axis coincidental with the reference axis, the hub having a means for rigidly clamping the hub to the second member of the machine at any rotational position of the hub relative to the second member of the machine, the hub additionally having means for positive radial attachment of the spring elements to the hub yielding very low hysteresis or energy loss characteristics when the spring elements are flexed relative to the hub;

the standoffs providing an interfacing means for attaching the springs to the backing plate, the standoffs being rigidly fastened to the backing plate, the standoffs having means for positive radial attachment of the springs to the standoffs yielding very low hysteresis or energy loss characteristics when the springs are flexed relative to the standoffs, the standoffs being bendable in the radial direction by an amount sufficient to allow the springs to shorten slightly in the radial direction as they flex; and the springs being fabricated of replaceable flat plates of high stress steel, the dimensions and shape of the springs being selected to provide the torsional compliance desired between the first and second members of the machine.

9. The flexure coupling of claim 8 wherein additionally the backing plate has a right circular cylindrical pilot protrusion centered on the reference axis for concentric registration of the backing plate with a mating hole on the first member of the machine.

10. The flexure coupling of claim 8 wherein the backing plate mounting means consists of slotted holes angularly spaced on a circle centered on the center of the backing plate, the slots extending in the tangential direction about the circle, and screws with washers to tighten the mounting plate to the first member of the machine at a desired rotational position of the backing plate with respect to the first member.

11. The flexure coupling of claim 8 wherein the means for rigidly clamping the hub to the second member of the machine is provided by a bored hole centered on the hub's central cylindrical axis, a radial slot running from the bored hole to the outside of the hub, and screws which act to reduce the slot thickness and clamp the hub by friction to a mating shaft on the second member of the machine.

12. The flexure coupling of claim 8 wherein the means for positive radial attachment of the springs to the hub is by screw attachment through the springs to plane surfaces located at angular increments about the hub's exterior cylindrical surface, the plane surfaces being located so that the springs are arranged substantially along radii extending from the reference axis, the handedness of the spring attachments to the hub being arranged so that flexure of the springs in a preferred direction causes the springs to be bent away from the screw heads and resulting in only very small friction losses.

13. The flexure coupling of claim 8 wherein the standoffs are rigidly fastened to the backing plate with screws through the standoffs, the screws running in a direction parallel to the reference axis and extending into mating threaded holes in the backing plate.

14. The flexure coupling of claim 8 wherein the means for positive radial attachment of the springs to the standoffs is by screw attachment through the springs to plane surfaces on the standoffs, the plane surfaces being located so that the springs are arranged substantially along radii of the reference axis, the handedness of the spring attachments to the standoffs being arranged so that flexure of the spring elements in a preferred direction causes the springs to be bent away from the screw heads and resulting in only very small friction losses.

15. The flexure coupling of claim 8 wherein the standoffs' small compliance in the radial direction is controlled by relieving the thickness of the standoffs in the region of the spring attachments and the losses associated with this compliance are reduced by undercutting the standoffs at the backing plate interface surfaces in the region of the spring attachments.

16. The flexure coupling of claim 8 wherein the high stress steel springs are made of clock spring steel.

17. The flexure coupling of claim 8 wherein the high stress steel springs consist of rectangular steel plates having thickness selected according to the desired torsional compliance of the flexure coupling.

18. The flexure coupling of claim 8 wherein the high stress steel springs have holes drilled in their ends for screw attachment at one end of each spring to the hub and at the other end to a standoff.

19. The flexure coupling of claim 8 wherein the rotational adjustment of the backing plate mounting means is effected by an adjustment ear adapted to be fastened to the first member of the machine, the adjustment ear having an adjustment screw adapted to cause the backing plate to rotate with respect to the first member of the machine when the adjustment screw is rotated on its axis.

* * * * *